United States Patent [19]

Liu et al.

[11] Patent Number: 6,022,990

[45] Date of Patent: Feb. 8, 2000

[54] METHOD FOR SYNTHESIZING METHYL ACRYLATE

[75] Inventors: Zhao-Tie Liu; Jia-Qi Zhang; Xian-Gui Yang, all of Chengdu, China

[73] Assignees: Chengdu Insitute of Organic Chemistry, Chinese Academy of Sciences, Chengdu; National Research and Engineering Centre for Coal Slurry Gasification and Coal Chemical Industry, Tengzhou, both of China

[21] Appl. No.: 08/990,788

[22] Filed: Dec. 15, 1997

[30] Foreign Application Priority Data

Dec. 18, 1996 [CN] China ............................ 96117838

[51] Int. Cl.⁷ .................................................. C07C 67/36
[52] U.S. Cl. .................................................. 560/207
[58] Field of Search ..................................... 560/206, 207

[56] References Cited

U.S. PATENT DOCUMENTS 2,882,298  4/1959  Luberoff et al. .

4,788,334  11/1988  Burke ................................ 562/522

OTHER PUBLICATIONS

J. Nemec et al., "Acrylic acid and derivatives", Kirk Othmer Encyclopedia of Chemical Technology 2nd Edition vol. 1, pp. 330–354, (prior to 1978).

Chem Abstracts 1989:153605, Wang et al, 1988.

*Primary Examiner*—Samuel Barts
*Attorney, Agent, or Firm*—Browdy and Neimark

[57] ABSTRACT

The present invention relates to a novel catalyst composition and a novel process for synthesizing methyl acrylate from methyl formate and acetylene, in which methyl formate reacts with acetylene in the presence of a main catalyst comprising one or more compounds selected from $RuCl_3$, $Ni(CH_3COO)_2$, $NiBr_2$, $NiI_2$, $NiSO_4$, $Ni(NO_3)_2$, $PdCl_2$, $CoCl_2$, $Rh_3(CO)_{12}$ and $RhCl_3$, and the catalyst promoter comprising one or more compounds selected from $CuSO_4$, NaI, KI and $CH_3I$, at a temperature of 120~240° C., and under reaction pressure of 1.0~10.0 MPa, a molar ratio of methyl formate to acetylene ranges form 0.1:1 to 20:1. The yield of methyl acrylate may reach to 63%.

11 Claims, No Drawings

METHOD FOR SYNTHESIZING METHYL ACRYLATE

FIELD OF THE INVENTION

The present invention relates to a novel route for synthesizing methyl acrylate.

BACKGROUND OF THE INVENTION

Methyl acrylate is an important monomer for the synthesis of high molecular polymer. It can readily polymerize with other monomers to produce various polymers with different excellent properties and uses, which have been used in making a series of products, such as paints, textile aids, adhesives, dispersing agents, flocculating agents, thickening agents, water absorbents, and is extensively applied in chemical industry, textile processing, leather processing, paper manufacturing, food industry and oil extraction.

Acrylic acid was first prepared by Josoph Redten Bach in 1843 (J. Ann. 47, 125,1843) by oxidation of acrylaldehyde in the presence of silver oxide. It did not draw more attention until when 1901 Otto Rohm discovered that the polymers of acrylic acid and its ester have important industrial applications. Methods for preparing acrylic acid and its ester has been developing rapidly since then.

In 1927, Rohm and Haas in Germany invented an industrial method for synthesizing acrylic acid and its ester from cyanoethanol (Kirk Othmer, "Encyclopedia of Chemical Technology" 2nd ed., vol.1, p286). In 1953 Reppe invented a method for synthesizing acrylic acid and its ester directly from acetylene, carbon monoxide, and water or alcohol in the presence of nickel carbonyl as catalyst (Jusfus Leibigs Ann. Der chemie 582, 1, 1953). However, it was hard to solve the problem of labor protection due to the toxicity of nickel carbonyl. This process was improved by BASF Co. later. In the improved method nickel bromide was used as a catalyst, but the reaction pressure was relatively higher. On the other hand acetylene is very dangerous when being treated under a high pressure and needs special safety means. In 1958, Celanese and BF Goodrich Co. in the USA set up a unit for producing acrylic acid by using propiolactone method. In the nineteen sixties, the preparation of acrylic acid via acrylaldehyde by direct oxidization of propylene was developed successfully (Chem. Tech. June, p350–355, 1973; Kroli kowski, W. Soc. Plastic Eng. 1031, September 1964), which speeds up the development of producing acrylic acid and its ester.

Up to now, the cyanoethanol and propiolactone methods have not been used in industry due to the toxicity of cyanide and propiolactone. There are two main methods for preparing methyl acrylate, the propylene oxidation method and carbonylation method of acetylene with CO, water or alcohol. With the developing of the chemical industry, the demand of methyl acrylate is increasing. Therefore, new synthetic processes have been continuously explored to satisfy the demand of enhancing production capacity of methyl acrylate in various areas which are rich in different raw materials.

SUMMARY OF THE INVENTION

The object of this present invention is to provide a novel catalyst composition and a novel process for synthesizing directly methyl acrylate from acetylene and methyl formate.

The object of the present invention is accomplished by synthesizing methyl acrylate in one stage from acetylene and methyl formate (MF) in organic solvent, in the presence of a catalyst and a main catalyst promoter at a temperature ranging from 120 to 240° C. and under a total reaction pressure within the range of 1.0 to 10.0 MPa.

DETAILED DESCRIPTION OF THE INVENTION

According to the present invention, methyl acrylate is synthesized in one stage from acetylene and methyl formate (MF) in organic solvent, in the presence of a main catalyst and a catalyst promoter at a temperature ranging from 120 to 240° C. and under a total reaction pressure within the range of 1.0 to 10.0 MPa.

In the said synthesis, the molar ratio of methyl formate to acetylene ranges from 0.1:1 to 20:1.

The said organic solvent used is single solvent or a mixture of two or more solvents selected mainly from dimethylformamide (DMF), acetone, toluene, methanol, benzene, tetrahydrofuran, chloroform and iodoform. The amount of the organic solvent used ranges from 1:1 for to 6:1 as the volume ratio of the solvent to methyl formate. The organic solvent is able to dissolve a portion of acetylene, which ensures a higher concentration of acetylene in the solvent under lower total pressure in order to accelerate the reaction.

The said pressure of acetylene in gas phase before the reaction is lower than 1.5 MPa in the system. The total reaction pressure affects greatly the selectivity to methyl acrylate in this process. In order to maintain a total reaction pressure in the reaction system within the range of 1.0 to 10.0 MPa, a dilute gas needs to be introduced. The dilute gas is one or a mixture of two or more gases selected from $N_2$, air, water steam, hydrogen and CO, and its amount used ranges from 0.1:1 to 10:1 (volume/volume) based on the amount of acetylene.

The said main catalyst is one or more compounds selected from $Ni(CH_3COO)_2$ [labeled $Ni(OAc)_2$], $NiCl_2$, $NiBr_2$, $NiI_2$, $NiSO_4$, $Ni(NO_3)_2$, $PdCl_2$, $CoCl_2$, $RuCl_3$, $Rh_3(CO)_{12}$ and $RhCl_3$, and its amount used ranges from 1.0 to 10% by weight based on the weight of methyl formate used. The said catalyst promoter is one or more compounds selected from NaI, KI, $CH_3I$, and $CUSO_4$, and its amount used ranges from 1:1 to 15:1 as molar ratio to the main catalyst.

This catalyst system has various functions, one is to catalyze the decomposition of methyl formate to CO and methanol, the other is to catalyze the reaction of acetylene with CO and methanol to produce methyl acrylate, so that methyl acrylate can be synthesized directly in one stage from acetylene and methyl formate, which facilitates industrial production.

The present invention is described in further details in connection with the following Examples, it must be understood that the examples are for purposes of illustration and shall not be construed as limiting the scope of this invention.

EXAMPLE 1

2.0 g of $Ni(OAc)_2$, 0.1 g of $CuSO_4$, 0.5 g of NaI, and 0.05 g of $RuCl_3$ were weighed respectively, dissolved in the solution of 20 ml of MF and 40 ml of DMF. The mixture was added into a 100 ml autoclave, introduced with acetylene until the pressure of the autoclave reached 1.0 MPa, introduced with $N_2$ until the pressure up to 7.0 MPa, then heated to 200° C., and the total pressure of the autoclave increased to 10.0 MPa. The reaction was performed under these conditions for 1 hour. The conversion of methyl formate was 65%, and selectivity to methyl acrylate was 42%.

EXAMPLE 2

0.1 g of $Rh_3(CO)_{12}$ and 0.05 g of NaI were weighed respectively, dissolved in a solution of 10 ml of MF and 50 ml of tetrahydrofuran. The mixture was added into a 100 ml autoclave, introduced and saturated with acetylene until the pressure of the autoclave reached 0.5 MPa, introduced with $N_2$ until the pressure up to 6.0 MPa, then heated to 190° C., and the total pressure of the autoclave increased to 8.0 MPa. The reaction was performed under these conditions for 4 hour. The conversion of methyl formate was 95%, and selectivity to methyl acrylate was 21%.

EXAMPLE 3

0.1 g of $RhCl_3$ and 0.04 g of KI were weighed respectively, dissolved in a solution of 30 ml of MF and 30 ml of methanol. The mixture was added into a 100 ml autoclave, introduced and saturated with acetylene until the pressure of the autoclave reached 0.8 M Pa, introduced with CO until the pressure up to 2.0 MPa, introduced with $N_2$ until the pressure up to 7.0 MPa, then heated to 170° C., and the total pressure of the autoclave increased to 9.0 MPa. The reaction was performed under these conditions for 3 hour. The conversion of methyl formate was 86%, and selectivity to methyl acrylate was 41%.

EXAMPLE 4

0.5 g of $PdCl_2$, 0.2 g of $CuSO_4$, and 0.5 g of NaCl were weighed respectively, and dissolved in a solution of 10 ml of MF and 60 ml of toluene. The mixture was added into a 100 ml autoclave, introduced and saturated with acetylene until the pressure of the autoclave reached 1.0 MPa, introduced with $N_2$ until the pressure up to 8.0 MPa, then heated to 200° C., and the total pressure of autoclave increased to 10.0 MPa. The reaction was performed under these conditions for 4 hour. The conversion of methyl formate was 75%, and selectivity to methyl acrylate was 32%.

EXAMPLE 5

1.0 g of $CoCl_2$, 0.1 g of $CuSO_4$, and 0.5 g of NaI were weighed respectively, and dissolved in a solution of 10 ml of MF and 50 ml of DMF. The mixture was added into a 100 ml autoclave, introduced and saturated with acetylene until the pressure of the autoclave reached 1.0 MPa, introduced with $N_2$ until the pressure up to 7.0 MPa, then heated to 200° C., and the total pressure of the autoclave increased to 8.0 MPa. The reaction was performed under these conditions for 4 hour. The conversion of methyl formate was 63%, and selectivity to methyl acrylate was 25%.

EXAMPLE 6

2.0 g of $Ni(OAc)_2$ and 0.5 of NaI were weighed respectively, dissolved in a solution of 10 ml of MF and 50 ml of DMF. The mixture was added into a 100 ml autoclave, introduced and saturated with acetylene until the pressure of the autoclave reached 0.5 MPa, introduced with CO until the pressure up to 3.5 MPa, introduced with $N_2$ until the pressure up to 7.0 MPa, then heated to 200° C., and the total pressure of the autoclave increased to 10 MPa. The reaction was performed under these conditions for 4 hour. The conversion of methyl formate was 70%, and selectivity to methyl acrylate was 90%.

EXAMPLE 7

1.0 g of $Ni(OAc)_2$, 0.1 g of $CuSO_4$, 0.5 g of NaI, and 0.05 g of $RuCl_3$ were weighed respectively, dissolved in a solution of 20 ml of MF and 40 ml of DMF. The mixture was added into a 100 ml autoclave, introduced and saturated with acetylene until the pressure of the autoclave reached 1.0 MPa, introduced with $N_2$ until the pressure up to 7.0 MPa, then heated to 200° C., and the total pressure of the autoclave increased to 10.0 MPa. The reaction was performed under these conditions for 4 hour. The conversion of methyl formate was 65%, and selectivity to methyl acrylate was 70%.

EXAMPLE 8

2.0 g of $Ni(OAc)_2$, 0.1 g of $CuSO_4$ and 0.5 g of NaI were weighed respectively, dissolved in a solution of 20 ml of MF and 40 ml of DMF. The mixture was added into a 100 ml autoclave, introduced and saturated with acetylene until the pressure of the autoclave reached 1.0 MPa, introduced with CO until the pressure up to 3.0 MPa, introduced with $N_2$ until the pressure up to 6.0 MPa, then heated to 180° C., and the pressure of the autoclave increased to 9.0 MPa. The reaction was performed under these conditions for 4 hour. The conversion of methyl formate was 60%, and selectivity to methyl acrylate was 65%.

EXAMPLE 9

2.0 g of $Ni(OAc)_2$, 0.1 g of $CuSO_4$ and 0.5 g of NaI were weighed respectively, dissolved in a solution of 20 ml of MF and 40 ml of DMF. The mixture was added into a 100 ml autoclave, introduced and saturated with acetylene until the pressure of the autoclave reached 1.0 MPa, introduced with CO until the pressure up to 3.0 MPa, introduced with $N_2$ until the pressure up to 7.0 MPa, then heated to 180° C., the total pressure of the autoclave increased to 9.0 MPa. The reaction was performed under these conditions for 4 hour. The conversion of methyl formate was 70%, and selectivity to methyl acrylate was 75%.

EXAMPLE 10

1.0 g of $Ni(OAc)_2$, and 0.1 g of $CuSO_4$ were weighed respectively, dissolved in a solution of 20 ml of MF and 40 ml of DMF. The mixture was added into a 100 ml autoclave, introduced and saturated with acetylene until the pressure of the autoclave reached 1.0 MPa, introduced with $N_2$ until the pressure up to 7.0 MPa, then heated to 170° C., and the pressure of the autoclave increased to 8.0 MPa. The reaction was performed under these conditions for 4 hour. The conversion of methyl formate was 41%, and selectivity to methyl acrylate was 56%.

EXAMPLE 11

1.0 g of $Ni(OAc)_2$, and 0.1 g of $CuSO_4$ were weighed respectively, dissolved in a solution of 20 ml of MF and 40 ml of acetone. The mixture was added into a 100 ml autoclave, introduced and saturated with acetylene until the pressure of the autoclave reached 1.0 MPa, introduced with $N_2$ until the pressure up to 7.0 MPa, then heated to 170° C., the total pressure of the autoclave increased to 8.0 MPa. The reaction was performed under these conditions for 4 hour. The conversion of methyl formate was 46%, and selectivity to methyl acrylate was 50%.

EXAMPLE 12

1.0 g of $Ni(OAc)_2$, 0.1 9 of $CuSO_4$, 0.2 g of KI, and 0.05 g of $RuCl_3$ were weighed respectively, and dissolved in a solution of 10 ml of MF, 20 ml of $CH_3OH$ and 30 ml of DMF. The mixture was added into a 100 ml autoclave, introduced and saturated with acetylene until the pressure of the autoclave reached 1.0 MPa, introduced with $N_2$ until the pressure up to 7.0 MPa, then heated to 120° C., and the total pressure of the autoclave increased to 8.0 MPa. The reaction was performed under these conditions for 4 hour. The conversion of methyl formate was 38%, and selectivity to methyl acrylate was 68%.

What is claimed is:

1. A method for synthesizing methyl acrylate, wherein methyl acrylate is synthesized directly from acetylene and methyl formate in the presence of a catalyst system comprising a main catalyst selected from the group consisting of $NiCl_2$, $NiBr_2$, $Ni(CH_3COO)_2$, $NiSO_4$, $Ni(NO_3)_2$, $CoCl_2$, $PdCl_2$, and mixtures thereof in an amount of from 1.0 to 10% by weight based on the weight of methyl formate used, and a catalyst promoter selected from the group consisting of $CuSO_4$, NaCl, and mixtures thereof in an amount of from 1:1 to 15:1 molar ratio to the main catalyst.

2. A method for synthesizing methyl acrylate according to claim 1, wherein the synthesis is performed at a reaction temperature ranging from 120 to 240° C.

3. A method for synthesizing methyl acrylate according to claim 1, wherein the synthesis is performed under a reaction pressure ranging from 1.0 to 10.0 MPa.

4. A method for synthesizing methyl acrylate according to claim 1, wherein the molar ratio of methyl formate to acetylene ranges from 0.1:1 to 20:1.

5. A method for synthesizing methyl acrylate according to claim 1, wherein synthesis is performed in a solvent selected from the group consisting of dimethylformamide, acetone, methanol, tetrahydrofuran, chloroform, iodoform, and mixtures thereof in an in an amount from 0.1:1 to 6:1 (volume/volume) as the ratio of solvent to methyl formate.

6. A method for synthesizing methyl acrylate according to claim 1, wherein synthesis is performed in the presence of dilute gas selected from the group consisting of $N_2$, water steam, CO, air, $H_2$, and mixtures thereof in an amount from 0.1:1 to 10:1 (volume/volume) based on amount of acetylene.

7. A method for synthesizing methyl acrylate directly from acetylene and methyl formate, comprising reacting acetylene and methyl formate at a temperature of 120–240° C. in the presence of an amount sufficient of a diluent gas to maintain a pressure of 1.0 to 10.0 MPa, said methyl formate being dissolved in an organic solvent capable of dissolving a portion of said acetylene, said reaction being carried out in the presence of a main catalyst selected from the group consisting of $NiCl_2$, $NiBr_2$, $Ni(CH_3COO)_2$, $NiSO_4$, $Ni(NO_3)_2$, $CoCl_2$, $PdCl_2$, and mixtures thereof and a catalyst promoter selected from the group consisting of $CuSO_4$, NaCl, and mixtures thereof, the molar ratio of said catalyst promoter to said main catalyst being from 1:1 to 15:1.

8. A method according to claim 7 wherein the molar ratio of methyl formate to acetylene is 0.1:1 to 20:1.

9. A method according to claim 7 wherein said main catalyst is present in said solvent in an amount from 1.0 to 10% by weight based on the weight of said methyl formate.

10. A method according to claim 7 wherein said solvent is selected from the group consisting of dimethylformamide, acetone, methanol, tetrahydrofuran, chloroform, iodoform and mixtures thereof in an amount from 0.1:1 to 6:1 (volume/volume) as the ratio of solvent to methyl formate.

11. A method according to claim 1 wherein said diluent gas is selected from the group consisting of $N_2$, water steam, CO, air, $H_2$, and mixtures thereof in an amount from 0.1:1 to 10:1 (volume/volume) based on amount of acetylene.

* * * * *